(12) United States Patent
Frivik (10) Patent No.: US 9,151,736 B2
(45) Date of Patent: Oct. 6, 2015

(54) QUALITY SENSOR APPARATUS (75) Inventor: Bjørn Frivik, Paradis (NO)

(73) Assignee: Wema Systems AS, Blomsterdalen (NO)

( * ) Notice: Subject to any disclaimer, the term of this patent is extended or adjusted under 35 U.S.C. 154(b) by 577 days.

(21) Appl. No.: 13/517,955

(22) PCT Filed: Dec. 21, 2010

(86) PCT No.: PCT/NO2010/000481
§ 371 (c)(1),
(2), (4) Date: Aug. 24, 2012

(87) PCT Pub. No.: WO2011/078692
PCT Pub. Date: Jun. 30, 2011

(65) Prior Publication Data
US 2013/0167622 A1    Jul. 4, 2013

(30) Foreign Application Priority Data
Dec. 21, 2009  (GB) .................................... 0922464.3
Jan. 12, 2010  (NO) .................................... 20100047

(51) Int. Cl.
G01D 18/00     (2006.01)
G01N 33/00     (2006.01)
F01N 3/20      (2006.01)
G01N 25/00     (2006.01)
G01N 27/00     (2006.01)
G01N 29/02     (2006.01)

(52) U.S. Cl.
CPC ............. *G01N 33/00* (2013.01); *F01N 3/208* (2013.01); *G01N 25/00* (2013.01); *G01N 27/00* (2013.01); *G01N 29/02* (2013.01); *F01N 2610/14* (2013.01); *F01N 2610/148* (2013.01); *F01N 2900/1818* (2013.01); *Y02T 10/24* (2013.01)

(58) Field of Classification Search
CPC ............................... G01D 18/00; G01V 13/00
USPC .......................................................... 73/1.01
See application file for complete search history.

(56) References Cited

U.S. PATENT DOCUMENTS

| | | | | |
|---|---|---|---|---|
| 5,114,859 A * | 5/1992 | Kagenow | ......................... | 436/50 |
| 5,208,147 A * | 5/1993 | Kagenow et al. | ................ | 435/14 |
| 7,122,152 B2 * | 10/2006 | Lewis et al. | ...................... | 422/50 |
| 2002/0090738 A1 * | 7/2002 | Cozzette et al. | .............. | 436/518 |

* cited by examiner

Primary Examiner — Hezron E Williams
Assistant Examiner — Rodney T Frank
(74) Attorney, Agent, or Firm — Gary L. Bush; Andrew Kurth LLP (57) ABSTRACT An apparatus (100) for measuring quality of a urea solution is operated with at least a portion of the apparatus inserted into the urea solution. The apparatus (100) includes a configuration of sensors (180, 190, 200) for measuring mechanical and electrical properties within a volume of the urea solution, the measurements of mechanical and electrical properties being mutually differently influenced by components present in the urea solution. A data processing arrangement (230) of the apparatus (100) is operable to process the measurements of mechanical and electrical properties for generating output data (120) indicative of a quality of the urea solution. The apparatus (100) is also capable of being adapted to measure qualities of other types of solution.

14 Claims, 7 Drawing Sheets

QUALITY SENSOR APPARATUS

FIELD OF THE INVENTION

The present invention relates to quality sensor apparatus for vehicles, for example on-road and off-road vehicles, as well as for industrial and marine installations including combustion engines, wherein the apparatus is operable to monitor the quality of urea solution (for example AdBlue, "Adblu", DEF) to exhaust treatment systems of such vehicles and installations. Moreover, the invention concerns methods of operating such quality sensor apparatus. Furthermore, the invention relates to vehicles, industrial facilities and marine facilities including the quality sensor apparatus.

BACKGROUND OF THE INVENTION

Contemporary combustion engines beneficially operate with combustion in their one or more combustion chambers occurring at a high combustion temperature for achieving more efficient engine operation. However, engine operation at high combustion temperatures has associated therewith generation of soot and nitrogen oxide exhaust products, for example nitrous oxides (NOx). Soot and nitrogen oxide exhaust products are hazardous materials when ejected into the environment. For reducing concentrations of exhaust pollutants to within limits defined by legislation, for example contemporary European legislation pertaining to exhaust emissions, vehicle manufacturers conventionally employ Selective Catalytic Reduction (SCR) and/or Exhaust Gas Recirculation (EGR) in their vehicles. SCR is effective for absorbing nitrous oxides whereas EGR ensures more complete oxidation of nitrogen oxides present in exhaust gases.

SCR operation is improved by using chemical agents which are transported and/or stored on vehicles, marine facilities and industrial facilities. For example, "AdBlue" and "DEF" are trade names for a chemical agent corresponding substantially to aqueous urea solution 32.5%. This solution is injected into exhaust gases of modern diesel engines during a post-combustion process for treating engine exhaust gases for reducing a proportion of harmful nitrous oxide (NOx) present in these gases. AdBlue, DEF, "Adblu" is only ever used in conjunction with an SCR. Moreover, vehicles which are equipped with an SCR will carry an AdBlue, DEF or "Adblu" storage tank in addition to a fuel tank. In operation, AdBlue, DEF, or "Adblu" is transferred from the storage tank and injected under pressure into exhaust gases where a series of chemical reactions occur as outlined in Table 1 below.

Figure 1:
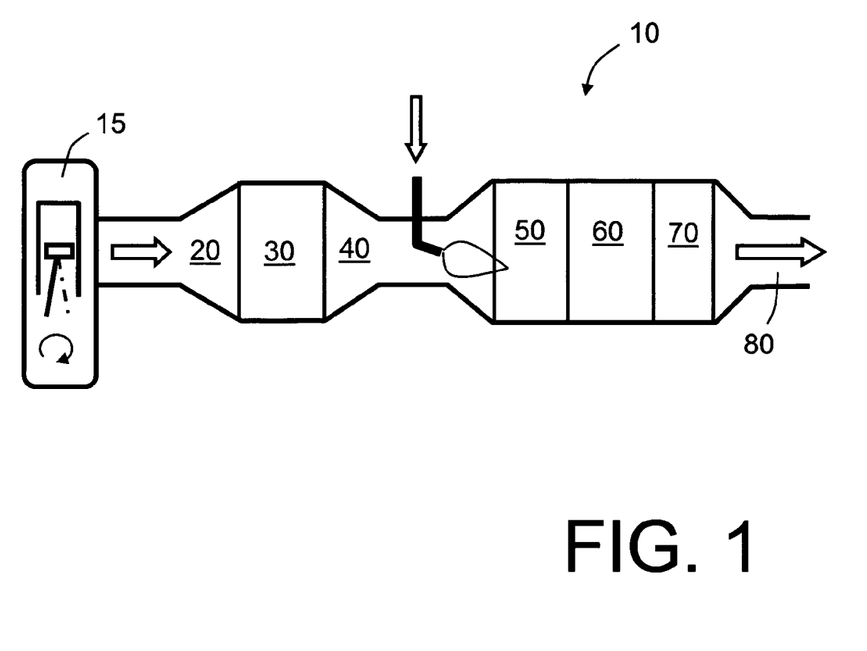
FIG. 1 is a schematic illustration of an exhaust system of a vehicle operable to employ AdBlue ("Adblu"), namely urea solution, for reducing NOx concentrations in exhaust gases passing through the exhaust system.

In FIG. 1, an exhaust system for a combustion engine 15 is indicated generally by 10. The system 10 includes in sequence an inlet 20 for receiving combustion gases from the engine 15, an oxidation catalyst 30, an AdBlue injection region 40, an hydrolysis catalyst 50, an SCR catalyst 60, an oxidation catalyst 70 and finally an outlet 80.

TABLE 1

| Region | Reaction |
|---|---|
| Oxidation catalyst 30 | $2NO + O_2 = 2NO_2$ |
| | $2CO + O_2 = 2CO_2$ |
| | $4HC + 3O_2 = 2CO_2 + 2H_2O$ |
| Hydrolysis catalyst 50 | $CO(NH_2)_2 + H_2O = 2NH_3 + CO_2$ |
| SCR catalyst 60 | $8NH_3 + 6NO_2 + 7N_2 + 12H_2O$ |
| | $4NH_3 + 4NO = O_2 + 4N_2 + 6H_2O$ |
| | $2NH_3 + NO + NO_2 = 2N_2 + 3H_2O$ |
| Oxidation catalyst 70 | $4NH_3 + 3O_2 = 2N_2 + 6\,H_2O$ |

Essentially, the process occurring in the exhaust system 10 involves an AdBlue mixture being passed onto a super-heated porous ceramic head of the SCR catalyst 60 whereat the de-ionised water evaporates and remaining urea of the injected AdBlue is passed on as a reagent which is operable to break nitrous oxide components (NOx) into mostly Nitrogen and water. Any contaminants present in the AdBlue will collect on the SCR catalyst 60, eventually causing it to clog and fail. It is therefore imperative that the AdBlue remains free from impurities through all stages of production, storage and dispensing.

Detection of ingredients in AdBlue, DEF or "Adblu" is highly desirable; detection of such ingredients is to be understood to be a quality measurement, not merely a measurement of urea concentration which is something different. Agricultural grades of urea are designated for use in agriculture, for example to improve soil quality, whereas industrial grades of urea, for example Adblue, DEF, are adapted for use in road vehicles, for example trucks and buses. When agricultural urea is cheaper on account of more contaminants therein in comparison to industrial AdBlue, there is a temptation for users to employ agricultural AdBlue in trucks and buses for exhaust gas treatment during road use in breach of legal regulations; impurities in agricultural grades of urea can potentially poison catalysts in exhaust systems as well as risk creating airborne pollution including, for example, heavy metals. Moreover, there is also a potential risk that agricultural urea or industrial AdBlue, DEF is contaminated by extraneous material on account of conditions of its storage, for example in unclean tanks which have previously employed to store other materials, for example insecticides.

Another risk is an unintentional confusion by personnel of different tanks available on a vehicle, wherein Diesel fuel, wind screen washer liquid and similar is filled into the Adblue, DEF tank by accident. Another risk is that personnel try to substitute Adblue, DEF with other materials, for example a saline solution, in Adblue, DEF tanks of vehicles to save money. Many farmers face extreme economic pressures which can result in them being attempted to save wherever feasible Unwanted contamination in Adblue, DEF can have other consequences, for example resulting in a catastrophic event such as a complete SCR failure. Attempting to operate vehicles with defective SCR can represent a criminal offence. AdBlue, DEF is very susceptible to contamination from both foreign matter and incorrect material selection. A main influence concerns the de-ionised water element of the solution which draws ions from materials which it comes into contact with; this changes the chemical composition of the AdBlue, DEF and causes salts to form which in turn clog the ceramic head on the SCR catalyst 60. Most common causes of premature failure of the SCR catalyst 60 are typically either a result of the ingress of damaged pump parts being accidentally transferred into the AdBlue tank or as a result of incorrect material selection. Inert materials should thus always be used to handle AdBlue.

Thus, poor quality of AdBlue can cause increased vehicle pollution and also damage to engine exhaust gas systems. It is not always possible for vehicle drivers to be certain about the origin of AdBlue, DEF that is utilized in their vehicles, and can in consequence unintentionally cause, for example, dangerous pollution from contaminants present in the AdBlue, DEF. However, devices for metering concentrations of urea solution are known, for example a device as described in published United States patent application US 2005/0011183A1 (Ripper et al.). The device includes a sensor unit for monitoring one or more physical state variables of an enzyme-free urea solution. The sensor unit is designed for detecting pH, a dielectric constant of the urea solution and/or conduction of the enzyme-free urea solution. Electrodes of the sensor unit are, for example, implemented as an intermeshed comb-like structure. Moreover, the sensor unit includes a vibration generator for testing mechanical properties of the urea solution, wherein the vibration generator includes a quartz oscillator and/or a piezoelectric crystal. It is to be appreciated that the device described in published United States patent application US 2005/0011183A1 (Ripper et al.) is essentially a urea solution concentration measureing device, which is very different to a urea solution quality measuring apparatus.

However, such known devices for metering urea solution concentration are not sensitive enough and/or accurate enough for distinguishing between various qualities of urea solution for vehicle use, for example distinguishing agricultural-grade urea from transport-grade urea due to presence of trace metal salts that hardly cause any perceptible change in urea solution concentration. Urea solution quality spatially varies within a vehicle urea tank and known sensors measure in a given spatial locality which is potentially not representative of the generally quality of the urea solution in the tank; thus, the aforementioned device described in published United States patent application US 2005/0011183A1 (Ripper et al.) would be unsuitable for constructing a urea quality monitoring apparatus.

SUMMARY OF THE INVENTION

The present invention seeks to provide a quality sensor apparatus which is operable to distinguish more accurately between various qualities of urea solution within a urea tank.

According to a first aspect of the present invention, there is provided an apparatus as claimed in appended claim 1: there is provided an apparatus for measuring quality of a urea solution into which at least a portion of the apparatus is inserted in operation, characterized in that the apparatus includes a configuration of sensors for measuring mechanical and electrical properties within a volume of the urea solution, the measurements of mechanical and electrical properties being mutually differently influenced by components present in the urea solution, and a data processing arrangement for processing the measurements of mechanical and electrical properties for generating output data indicative of a quality of the urea solution.

The invention is of advantage in that the quality of the urea solution is susceptible to being measured with greater accuracy and reliability.

Optionally, in the apparatus, the configuration of sensors includes acoustic and conductivity sensors for measuring mechanical and electrical properties respectively, the sensors being spatially deployed spaced apart within the apparatus.

Optionally, in the apparatus, the sensors include a thermometer for measuring a temperature (T) of the urea solution, and for providing the data processing arrangement data corresponding to the temperature (T) for use in computing the quality of the urea solution.

Optionally, in the apparatus, the configuration of sensors includes an electrical conductivity sensor for measuring an electrical conductivity of the urea solution, the conductivity sensor including a configuration of electrodes disposed in a flow tunnel for receiving the urea solution, the flow tunnel being operable to electrically screen the configuration of electrodes from external influences spatially outside the tunnel. More optionally, in the apparatus, the configuration of electrodes includes electrodes disposed in a linear arrangement along the flow tunnel. More optionally, in the apparatus, an outer set of electrodes ($P_1$) near ends of the flow tunnel are operable to be excited to generate an interrogating electric field within the tunnel and an inner set of electrodes ($P_2$) near a central region of the flow tunnel are operable to generate a received signal for conveying to the data processing arrangement. Optionally, in the apparatus, the configuration of electrodes ($P_1$, $P_2$) includes at least one of: stainless steel electrodes, carbon electrodes, silver electrodes. Optionally, in the apparatus, the data processing arrangement is operable to apply at least one of alternating (a.c.) signals and static (d.c.) signals to the configuration of electrodes when in operation for determining at least one of static conductivity and complex conductivity of the urea solution for use in determining its quality.

Optionally, in the apparatus, the configuration of sensors includes an acoustic sensor including an acoustic transducer arrangement disposed in a spaced apart manner from a corresponding acoustic reflector, wherein the transducer arrangement is operable to generate one or more acoustic pulses which propagate through the urea solution, are reflected from the reflector and are subsequently received back at the transducer arrangement for generating a received signal for the data processing arrangement to process for determining a density of the urea solution.

Optionally, the apparatus further includes a mounting flange for mounting the apparatus to a urea solution tank, a heater arrangement for heating the urea solution, and a urea solution level sensing arrangement for sensing a surface height of the urea solution relative to the apparatus.

According to a second aspect of the invention, there is provided a method of measuring a quality of a urea solution by using an apparatus, characterized in that the method includes:

(a) arranging for at least a portion of the apparatus to be inserted in operation into the urea solution;

(b) measuring using a configuration of sensors of the apparatus for measuring mechanical and electrical properties within a volume of the urea solution, the measurements of mechanical and electrical properties being mutually differently influenced by components present in the urea solution; and (c) processing using a data processing arrangement the measurements of mechanical and electrical properties for generating output data indicative of a quality of the urea solution.

According to a third aspect of the invention, there is provided a software product recorded on a machine readable medium, the software product being executable on computing hardware for implementing a method pursuant to the second aspect of the invention.

According to a fourth aspect of the invention, there is provided an apparatus for measuring quality of a solution into which at least a portion of the apparatus is inserted in operation, characterized in that the apparatus includes a configuration of sensors for measuring mechanical and electrical properties within a volume of the solution, the measurements of mechanical and electrical properties being mutually differently influenced by components present in the solution, and a data processing arrangement for processing the measurement of mechanical and electrical properties for generating output data indicative of a quality of the solution.

According to a fifth aspect of the invention, there is provided a method of measuring a quality of a solution by using an apparatus, characterized in that the method includes:
(a) arranging for at least a portion of the apparatus to be inserted in operation into the solution;
(b) measuring using a configuration of sensors of the apparatus for measuring mechanical and electrical properties within a volume of the solution, the measurements of mechanical and electrical properties being mutually differently influenced by components present in the solution; and
(c) processing using a data processing arrangement the measurements of mechanical and electrical properties for generating output data indicative of a quality of the solution.

It will be appreciated that features of the invention are susceptible to being combined in various combinations without departing from the scope of the invention.

DESCRIPTION OF THE DIAGRAMS

Embodiments of the present invention will now be described, by way of example only, with reference to the following diagrams wherein.

In the accompanying diagrams, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DESCRIPTION OF EMBODIMENTS OF THE INVENTION

The preset invention is concerned with providing a quality sensor apparatus for measuring solution quality within a representative spatial region of the solution, for example a urea solution present within a storage tank, by using a spatially distributed combination of sensors integrated to an apparatus assembly; the apparatus is operable to measure solution characteristics within an extensive volume of the solution. Such an apparatus is in contradistinction to known devices for measuring urea solution concentration characteristics by implementing a measurement at a specific spatial point within a tank containing urea solution in operation. Beneficially, measurement of ureea solution quality is achieved by determining a velocity of acoustic radiation propagating within an extensive spatial volume of the solution, most advantageously utilizing reflected acoustic radiation to increase an effective propagation path length. Moreover, measurement of electrical conductivity of urea solution is beneficially implemented using a configuration of electrodes in an extensive spatial configuration providing enhanced measurement accuracy through a significance spatial region of the solution. Optionally, alternating current (a.c.) measurements are performed to assist to characterize quality-indicative properties of the urea solution. More optionally, such a.c. measurements are performed at frequencies corresponding to dipole moments of ions present in solution, thereby enabling the nature of the ions to be determined and hence an indication of types of impurities present in the solution. Optionally, direct current (d.c.) measurements are performed to assist to characterize quality-indicative properties of the urea solution. Optionally, combinations of a.c. and d.c. measurements are utilized for measuring the quality of the solution. Both urea solution density and urea solution electrical conductivity are a function of urea solution temperature which is also monitored in the quality sensor apparatus. Density and electrical conductivity measurements of a urea solution, optionally as a function of temperature, are employed as input parameters to a mapping function whose output parameter is an indication of quality of the urea solution; such an indication of quality should not be confused with concentration measurement which is another issue. The mapping function is beneficially implemented using one or more software products stored on machine-readable media, the products being executable on computing hardware of the apparatus to provide the mapping function. Moreover, the mapping function is optionally implemented as a lookup table, an interpolated polynomial representation and/or as a mathematical model embodying formulae representing measurement processes utilized in the apparatus. Optionally, the mapping function is implemented as a neural-network type function implemented in software.

Figure 2A:
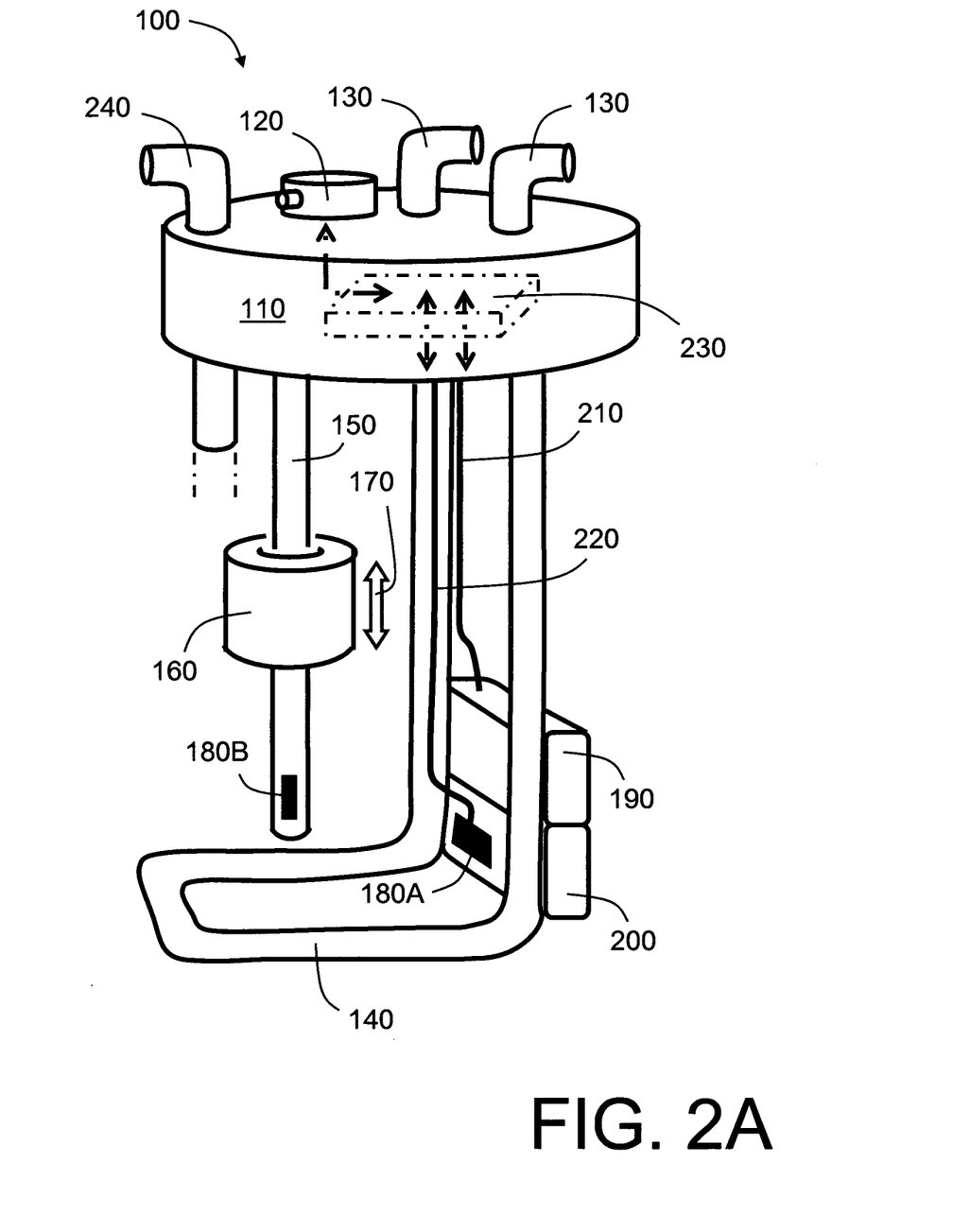
FIG. 2A to FIG. 2C are schematic illustrations of embodiments of a quality sensor apparatus pursuant to the present invention.
Figure 2B:
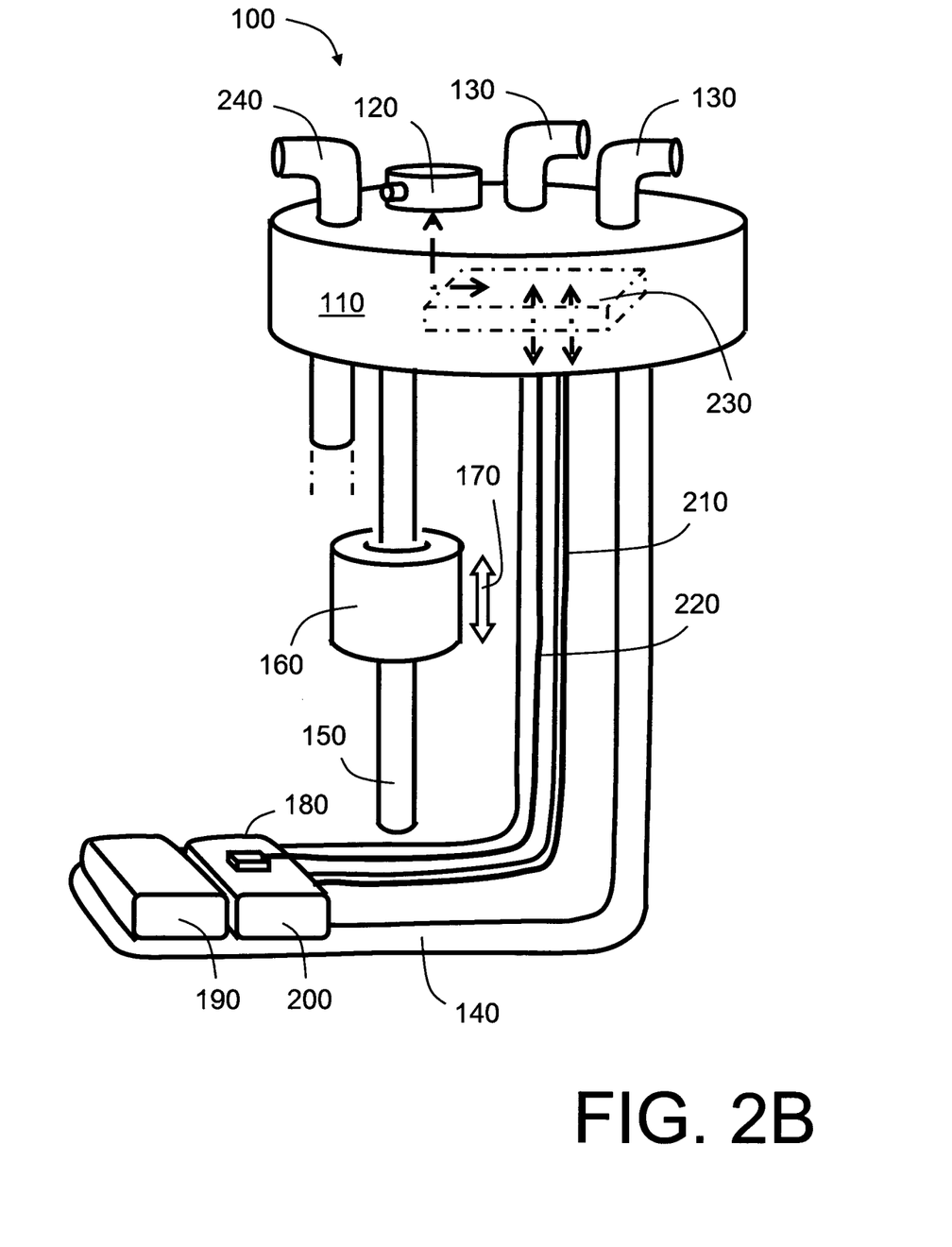
Figure 2C:
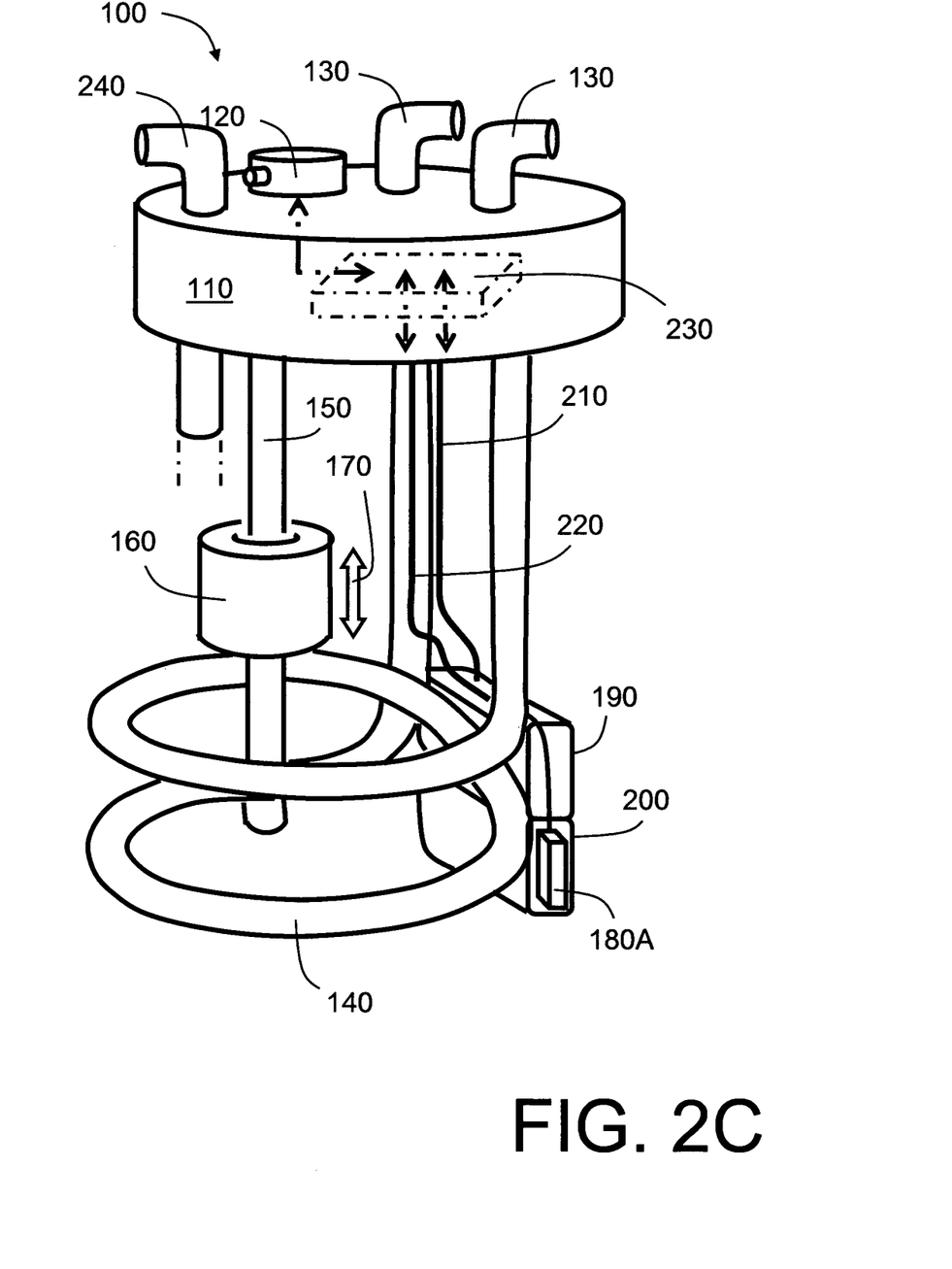

Implementations of the apparatus will now be described with reference to FIG. 2A, FIG. 2B and FIG. 2C. In FIG. 2A, the apparatus is indicated generally by 100 and comprises a flange 110 including an electrical connector 120 for receiving power and providing input and output signals to and from the apparatus 100 respectively. Moreover, the apparatus 100 includes pipe connections 130 for receiving hoses for heating water for heating a urea solution into which a heating coil or heating loop 140 of the apparatus 100 is at least partially immersed in operation. The flange 110 is adapted for enabling the apparatus 100 to be mounted to a hole provided in a urea solution tank (not shown). Optionally, the tank is mounted on a road vehicle, wherein the tank is operable to store urea solution to be injected into an exhaust system of the vehicle for treating NOX combustion products generated in operation by a combustion engine of the vehicle. The flange 110 is further provided with one or more tube connections and associated tubes denoted by 240 through the flange 110 for adding, removing and/or recirculating urea solution, as well as providing venting.

The apparatus 100 further comprises a urea solution level meter comprising a sensor tube 150 provided with an associated float 160. The float 160 is operable to float on an upper surface of a volume of urea solution. Moreover, the float 160 includes one or more permanent magnets, and the sensor tube 150 includes a spatial series of magnetic reed relays disposed therealong which are selectively actuated in operation in response to the float 160 moving along the sensor tube 150 as denoted by an arrow 170 Additionally, the apparatus 100 includes one or more temperature sensors 180A, 180B, for example implemented as a thermocouple and/or a thermistor. The temperature sensor 180A is beneficially in close spatial proximity to sensors 190, 200 of the apparatus 110, and the temperature sensor 180B is beneficially mounted onto the sensor tube 150.

At a lower end of the heating coil or heating loop 140 are mounted an acoustic sensor 190 for measuring density of the urea solution, and also an electrical conductivity sensor 200. In FIG. 2B, the sensors 190, 200 are positioned at a distal end of an extensive "L" heating loop 140. The acoustic sensor 190 and the conductivity sensor 200 are spatially separate, optionally disposed in an adjacent butting configuration, and are operable to characterize a urea solution by measuring within a significant portion of a volume of the urea solution tank in contradistinction to contemporary urea solution measuring devices which perform a measurement at only a spatial point locality. Output signals from the sensors 180A, 180B, 190, 200 are conveyed via signal cables 210, 220 to a data processing unit 230 including computing hardware, for example a microcontroller, operable to execute one or more software products stored on machine readable media, for example solid state read/write data memory, for enabling the computing hardware to process the output signals conveyed via the cables 210, 220 to generate a measurement output available at the electrical connector 120. In FIG. 2C, the heating loop 140 is implemented as a spiral structure comprising one or more turns; a spiral is potentially more compact and provides a greater heating surface area, thereby more rapid heating of the urea solution. Conversely, an extensive L-loop implementation of FIG. 2B provides heating in a larger spatial volume.

As described briefly in the foregoing, the density ρ and electrical conductivity S of a urea solution is describable in general terms from Equations 1 and 2 (Eq.1 and Eq. 2):

$$\rho = F_1(T, K, q) \qquad \text{Eq. 1}$$

$$S = F_2(T, K, q) \qquad \text{Eq. 2}$$

wherein
  T=temperature;
  K=concentration of urea in solution in a tank;
  q=concentration of impurities present in the tank;
  $F_1$=first function providing density as an output;
  $F_2$=second function providing electrical conductivity as an output.

Figure 3:
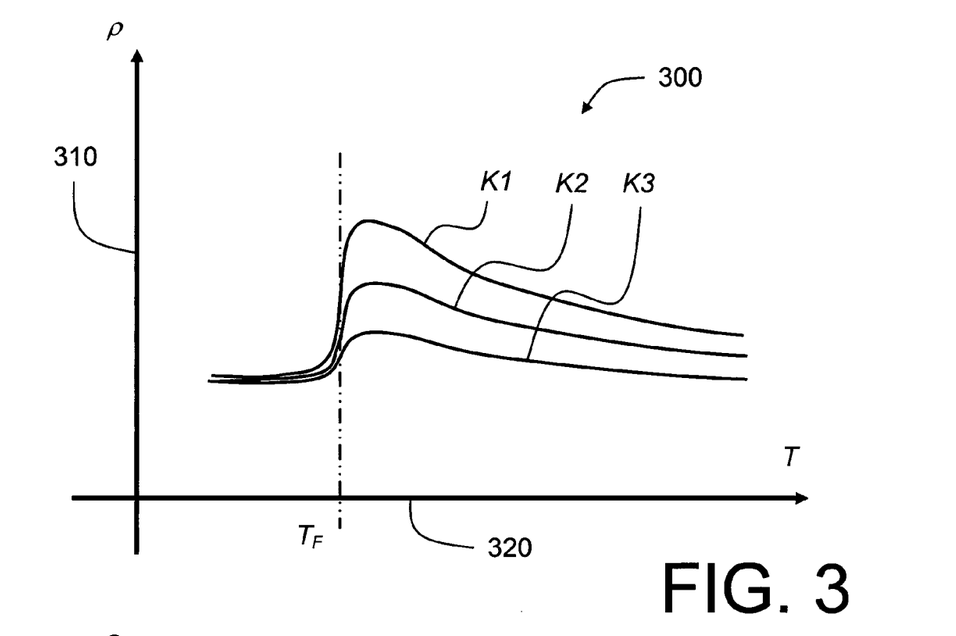
FIG. 3 is a schematic illustration of density characteristics of a urea solution.

Referring to FIG. 3, there is shown in qualitative manner, in a graph indicated generally by 300 and including an abscissa axis 320 denoting increasing temperature from left to right and an ordinate axis 310 denoting increasing density from bottom to top, a variation of the density ρ as a function of the different concentrations of urea K and temperature T of the urea solution. Below a transition temperature $T_F$, urea freezes out of the solution and the volume of the frozen solution expands. Above the transition temperature $T_F$, the urea solution exhibits properties which become more akin to plain water. A concentration $K_1$ corresponds to a greater concentration of urea in water In comparison to a concentration $K_2$; similarly, the concentration $K_2$ corresponds to a greater concentration of urea in water In comparison to a concentration $K_3$. The density ρ is sensed in the apparatus 100 by measuring a propagation delay of a pulse burst of ultrasonic radiation through the urea solution in the tank; for a given propagation path of length L within the urea solution in the tank, the propagation delay Δt is inversely proportional to acoustic velocity v of the acoustic pulse, namely as defined by Equation 3 (Eq. 3):

$$\Delta t = \frac{L}{v} \qquad \text{Eq. 3}$$

Beneficially, on account of a relatively compact nature of the apparatus 100, in order to include enough oscillations to define a pulse precisely within a Fourier domain, the pulse burst preferably includes a few cycles of acoustic radiation having a frequency in a range of 300 kHz to 10 MHz, more preferably in a range 700 kHz to 3 MHz, and most preferably substantially 1 MHz. In an event that a single pulse is utilized, its pulse length is thus beneficially in an order of 1 μsec duration. Knowing the temperature T and the propagation delay Δt, the density ρ can be computed from Equation 4 (Eq. 4):

$$\rho = F_3(R, \Delta t) \qquad \text{Eq. 4}$$

A combination of Equations 3, 4 and 1 can be used to determine a combined contribution of the concentration of urea K and an indication of the impurities q. These functions can be derived from theoretical analysis or determined numerically, for example as a lookup table with interpolation or as a polynomial representation, from experimental results from various known calibration urea solutions.

The speed of sound in a non-gaseous medium takes into account non-zero stiffness both for volumetric and shear deformations. It is thus feasible to generate sound waves with different velocities depending upon which deformation mode is utilized. Sound waves generating volumetric deformations, namely compressions, and shear deformations are referred to as longitudinal and shear waves respectively. In Earthquakes, corresponding seismic waves are referred to as P-waves and S-waves respectively. The sound velocities of these two types of waves are provided in Equations 5 and 6 (Eq. 5 & Eq. 6):

$$c_p = \sqrt{\frac{K_B + \frac{4}{3}G}{\rho}} = \sqrt{\frac{E(1-v)}{\rho(1+v)(1-2v)}} \qquad \text{Eq. 5}$$

$$c_s = \sqrt{\frac{G}{\rho}} \qquad \text{Eq. 6}$$

wherein
  $K_B$ and G are bulk modulus and shear modulus of the urea solution respectively;
  $c_p$=velocity of volumetric wave;
  $c_s$=velocity of shear wave;
  E=Young's modulus; and
  v=Poisson's ratio.

It will be appreciated that density of the urea solution is not sufficient in itself to characterize the quality of the urea solution when other contaminants are also present, for example metallic salts. Such metallic salts can represent a pollution hazard when ejected from an exhaust system of a vehicle and can also result in catalyst poisoning in vehicle exhaust systems. Such catalysts can include noble metals which are expensive to replace. It is therefore important to identify when an inferior grade of Adblue, DEF has been employed which could risk damaging by poisoning catalytic components of a vehicle exhaust treatment system.

Figure 4:
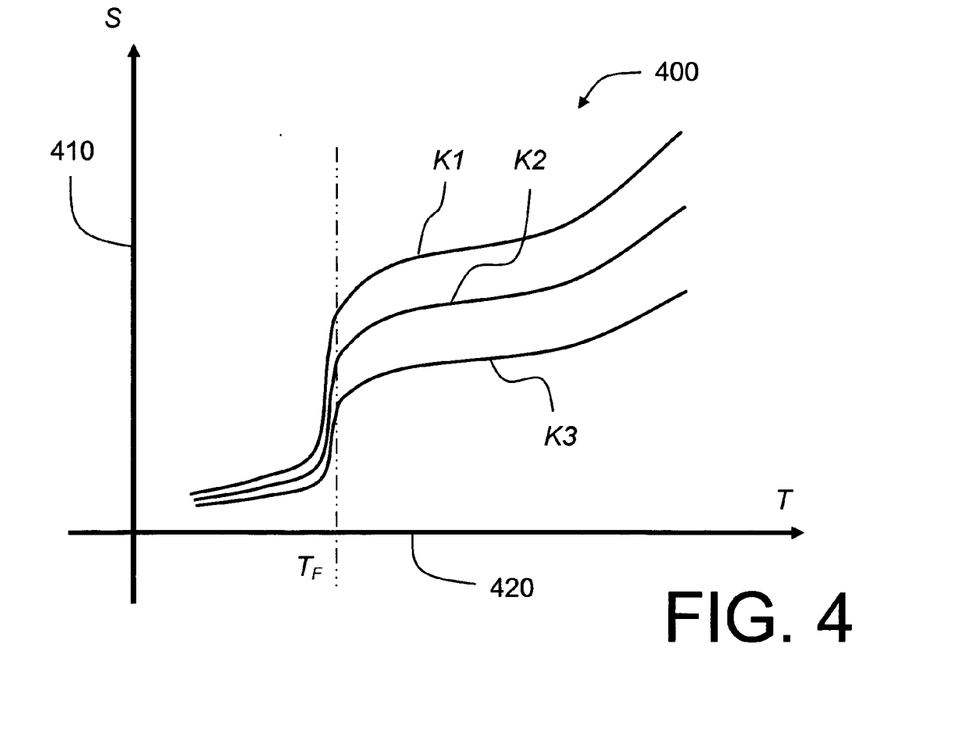
FIG. 4 is a schematic illustration of conductivity measurements of a urea solution.

Although the acoustic sensor 190 is susceptible to being used to determine urea solution density ρ via sound velocity measurement, such measurement is not sufficient in itself to determine a presence of other trace contaminants which may also be present in the urea solution, for example diverse metal salts. In order to obtain further information regarding these other trace contaminants, the conductivity sensor 200 is employed by the apparatus 100. Conductivity Sofa solution generally increases with temperature T because increasing temperature T causes more dissociation between ions within the urea solution as illustrated in FIG. 4; in FIG. 4, there is shown a graph indicated generally by 400 including an abscissa axis 420 denoting increasing temperature T from left to right and an ordinate axis 410 denoting increasing conductivity S from bottom to top. Moreover, the electrical conductivity S of a urea solution is also determined by a concentration of urea in the solution as well as impurities such as metallic salts present in the solution. A given concentration of urea solution at a given temperature should have a corresponding density ρ and a corresponding electrical conductivity S; when such density ρ and conductivity S as a function of temperature T deviate from what is expected, such deviation is indicative of the presence of contamination q.

The conductivity S is susceptible to being measured using alternating signals (a.c.), for example via capacitive coupling. Optionally, direct current (d.c.) signals can be employed, either alone or in combination with applied a.c. signals. Depending upon a nature of electrodes used to make contact with the urea solution, either an ohmic or electropotential (junction) contact is made to the urea solution. For example, carbon and silver electrodes are capable of making an ohmic contact to the solution, whereas metals such as stainless steel are observed to make an electropotential contact with the solution. Whereas ohmic contacts result in a constant resistance as a function of a potential difference between test electrodes to measure conductivity of a urea solution, electropotential contacts result in a varying resistance as a function of the potential difference applied between the electrodes. This varying resistance as a function of potential difference is influenced by trace metal salt contaminants present in the urea solution and can optionally be used to determine a concentration of trace salts present in the urea solution, namely to derive an indication of the quality of the urea solution. When a.c. signals are employed to measure conductivity of the urea solution and relatively high electrode potential are used which greatly exceed any electropotential (junction) contact, the influence of such a an electropotential (junction) becomes less significant.

Conductivity of a urea solution using alternating signals (a.c.) concerns complex impedances which vary as a function of frequency. Optionally, a.c. measurement of conductivity is performed in the apparatus at a frequency in a range of 100 Hz to 10 kHz, for beneficially substantially 5 kHz which is convenient for low-power electronic circuits to process. For example, an a.c. frequency of 5.1 kHz is conveniently employed. When a frequency of the alternating signals is in a regime of 100 kHz to 10 MHz, ionic dipole moments in the urea solution become significant and are clearly detectable in measured complex impedance as a function of temperature. Such complex impedances have been reported in an academic paper "*Frequency dependence of ionic conductivity of electrolyte solutions*", Chandra & Bagchi in association with research supported by the Council of Scientific and Industrial Research (CSIR), Department of Science and Technology (DST), and Government of India and Indian National Science Academy. This document is in the public domain and its contents are hereby incorporated by reference. The complex impedance of the urea solution is also influenced by contaminants such as metallic salts present in the solution.

Thus, the apparatus 100 via the conductivity sensor 200 is operable to measure d.c. conductivity and/or a.c. conductivity of the urea solution in the tank as a function of temperature T as denoted by Equation 2 (Eq. 2) in the foregoing:

$$S = F_2(T, K, q) \qquad \text{Eq. 2}$$

wherein
K=concentration of urea solution;
T=temperature of the urea solution; and
q=concentration of impurities present in the tank.

As aforementioned, Equations 1 and 2 represent two simultaneous equations with two unknown factors concentration K and impurity q contributing to conductivity S and density ρ, which enables the these unknown factors to be computed. Measurement of the conductivity at a.c. frequencies and/or determination of conductivity with electrodes giving rise to electropotential measurements enables further simultaneous equations to be established, enabling factor K and q to be more accurately determined. Both impurity q and concentration K enable the overall quality and suitability for use of the urea solution in the tank to be monitored. The simultaneous equations are beneficially solved by at least one of: lookup tables, polynomial representations.

Figure 5:
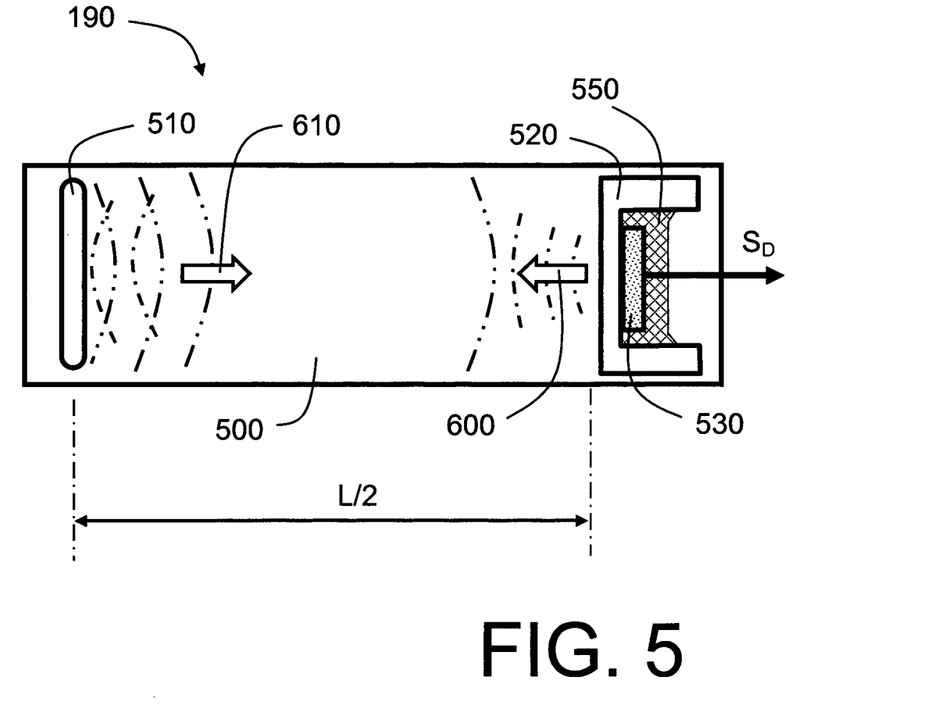
FIG. 5 is a schematic illustration of an acoustic sensor of the apparatus of FIG. 2.

The acoustic sensor 190 and the conductivity sensor 200 will now be described in more detail with reference to FIG. 5 and FIG. 6 respectively. In FIG. 5, the acoustic sensor 190 includes an elongate support panel 500 bearing an acoustic reflector 510 substantially at a first end of the panel 500. At a second end of the panel 500, remote from the first end, there is included a transducer arrangement comprising a housing 520 having an opening directed away from the reflector 510 as illustrated. The transducer arrangement further includes a piezo-electric element 530 implemented as a ceramic material disc, a quartz material disc and/or an organic polymer material disc. The element 530 is coupled to the urea solution in operation via the housing 520. Optionally, the housing 520 is fabricated from metal, a robust polymeric material, for example polyurethane, PTFE or similar, or from a ceramic material. Moreover, the element 530 is sealed and protected within the housing 520 by a region of chemically inert acoustic-energy-absorbing material 550, for example implemented as an appropriate grade of epoxy resin or other polymeric material. In operation, a pulse signal is applied via one or more electrodes $S_D$ to the element 530 to generate of an outward acoustic pulse series 600 which propagates along an elongate axis of the panel 500 to impinge upon the reflector 510 and to be then subsequently reflected therefrom as a reflected acoustic pulse series 610 which propagates back to the transducer arrangement to generate an echo signal in at the one or more electrodes $S_D$. Optionally, the element 530 is furnished with at least a pair of electrodes; a potential difference applied between the pair of electrodes establishes an electric field in the element 530, thereby causing stress which results in strain deformation of the element 530 and generation of associated acoustic radiation; a stress applied to the element 530 is also capable of generating an electric field within the element 530 which is detectable as a potential difference across the pair of electrodes. More optionally, the element 530 is furnished with separate electrodes for receiving drive signals and for outputting received echo signals. The data processing unit 230 is operable to generate a drive signal for the one or more electrodes $S_D$ and to receive reflected signals for processing. The acoustic sensor 190 is required to provide many years of reliable service when in contact with urea solution which can be corrosive. It is thus to be appreciated that the acoustic sensor 190 is not a simple assembly to design, and materials used for its construction have been selected with great care and attention to achieve reliable performance over many years of use. For example, stresses are reduced within the acoustic sensor 190 which could otherwise result in cracking of the element 530; such reduction in stress is feasible, for example, by employing laterally slidable surfaces for interfacing onto the element 530.

Figure 6:
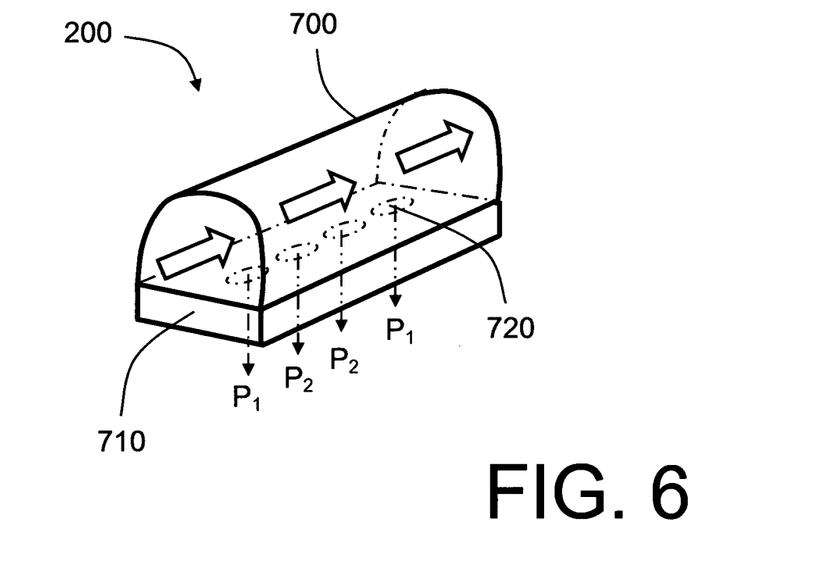
FIG. 6 is a schematic illustration of a conductivity sensor of the apparatus of FIG. 2A to 2C.

The conductivity sensor 200 is shown in greater detail in FIG. 6 and includes an elongate tunnel housing 700 fabricated from insulating plastics material with open ends for receiving a flow of urea solution through the housing 700 as denoted by arrows for a first flow direction; flow through the housing 700 can also occur in operation in an direction opposite to that shown. Moreover, the housing 700 is mounted onto a base 710 also fabricated from insulating plastics material. Along the base 710 are disposed a series of four electrodes 720 denoted by $P_1$ for outer electrodes and $P_2$ for inner electrodes. Optionally, the electrodes 720 are implemented using stainless steel material.

Figure 7:
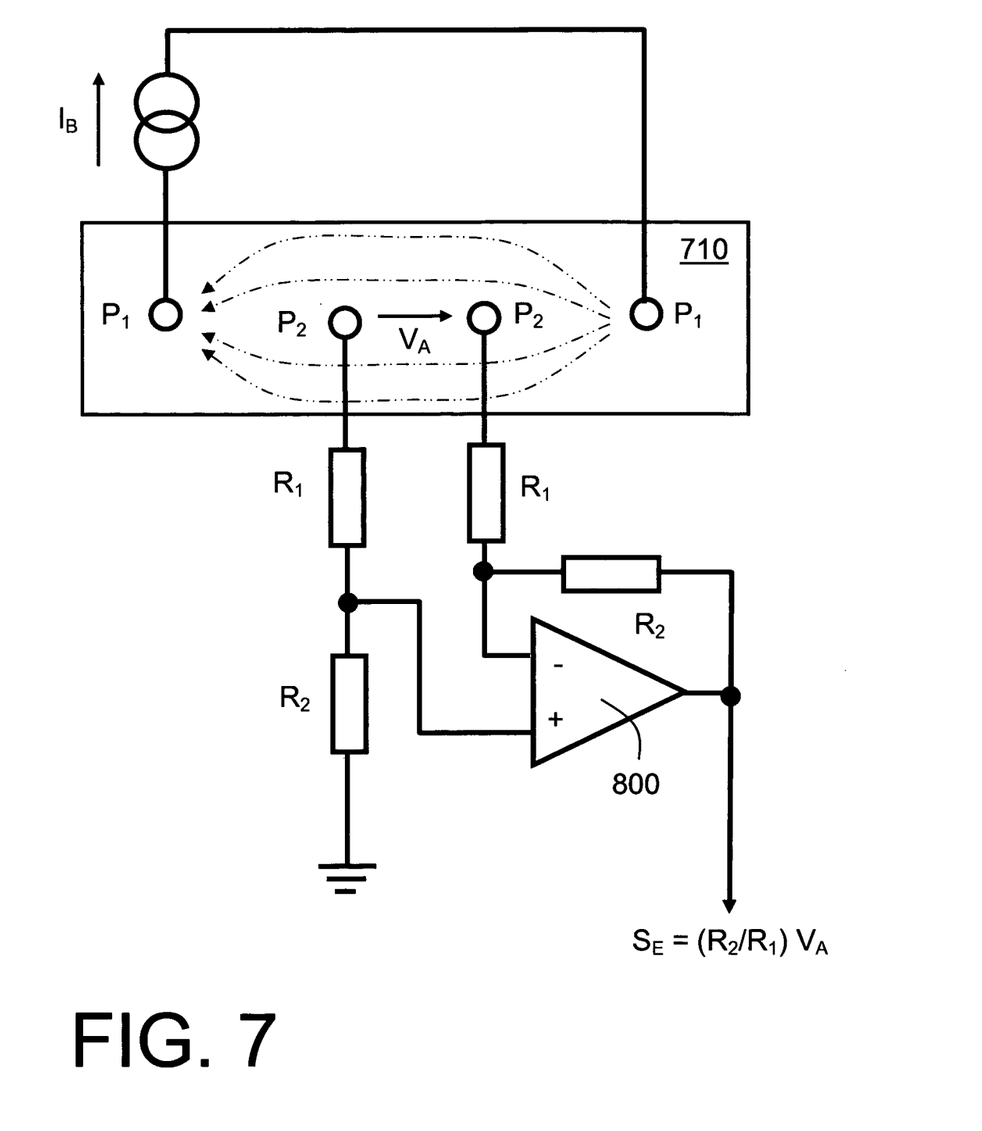
FIG. 7 is a circuit configuration for use with the conductivity sensor of FIG. 6.

In operation, when performing a.c. measurement of the conductivity S, an a.c. energizing signal current $I_B$ from a modulated current source established by the data processing unit 230 across the electrodes $P_1$ to generate an electric field along the housing 700 which is detected by the electrodes $P_2$ as a potential difference $V_A$, the electrodes $P_2$ being coupled via resistors $R_1$, $R_2$ to an operational amplifier 800 to generate a differential signal $S_E$ which is coupled to an analogue sampling input of the data processing unit 230. As the conductivity of the urea solution in the housing 700 varies, current flowing between the electrodes $P_1$ as a result of the bias current $I_B$ follows a spatial distribution within the housing 700 which is modulated as a function of the conductivity of the urea solution which influences the differential signal accordingly. Thus, the signal $S_E$ is a monotonic representation of the concentration K of urea in the urea solution. The data processing unit 230 is operable to receive the signal $S_E$, to convert it to data, and then to use this data to determining conductivity of the urea solution and hence a measure of its quality.

Optionally, the bias current $I_B$ optionally includes an a.c. signal component and/or is an a.c. signal. Moreover, the a.c. signal component and/or a.c. signal induces an alternating electric field within the housing 700 which interacts with dipole moments of ions in the urea solution. In consequence, the potential difference $V_A$ is an alternating signal which is amplified by the amplifier 800 and which is then subject to synchronous demodulation within the data processing unit 230 for determining a complex impedance for the urea solution. Beneficially, such synchronous demodulation is synchronized to a waveform applied to the electrodes $P_1$ to generate in-phase and quadrature signal components from the potential difference $V_A$ whose relative magnitudes are susceptible to being used within the data processing unit 230 for more accurately determining the magnitude of the impurities q. Such a.c. measurement of conductivity S of the urea solution provides insight with regard to impurities, for example metal salts, present in the urea solution as elucidated in the foregoing. Optionally, the sensors 190, 200 are operated temporally alternately to avoid signal cross-talk therebetween, thereby improving measuring accuracy of the apparatus 100.

The apparatus 100 is distinguished from previous manners of measuring urea solution characteristics on account of an high measurement accuracy, high robustness and great ease of use of the apparatus. On account of providing a measurement over a larger spatial volume, the apparatus 100 is operable to provide a more representative indication of urea solution quality in comparison to earlier approaches. The apparatus 100 is capable of being used to measure qualities of both enzyme-containing urea solution as well as enzyme-free urea solution. Optionally, the apparatus 100 is capable of being adapted to measure qualities of other type of solution in addition, or as an alternative to, quality of urea solution Thus, although the apparatus 100 in the foregoing is described in relation to measuring quality of urea solution in relation to road vehicles, off-road vehicles, in industrial applications such as stationary generator sets, in aircraft and in marine applications, the apparatus 100 is susceptible to being adapted to measure other types of solution and their associated quality characteristics, for example in oil industries, chemical processing industries, in food processing industries, in pharmaceutical industries, in water treatment industries, in fish cultivation industries, and so forth. In order to address such industries, complex impedance measurements executed by the data processing unit 230 in cooperation with the conductivity sensor 200 are a useful asset. Optionally, the apparatus 100 is furnished with other types of chemical sensors, for example electrochemical sensors and/or optical sensors, for example coupled to the data processing unit 230, for undertaking more complex solution quality monitoring tasks.

The data processing unit 230 is operable to perform a mapping function between signals that it receives from its sensors 180, 190, 200 and output that it provides indicative of quality of a solution into which the apparatus 100 is at least partially inserted. The mapping function is beneficially implemented in the data processing unit 230 via one or more executable software products recorded on data media, for example in solid state data memory. The software products are operable to provide the mapping function:

(a) by way of a lookup table;
(b) by way of one or more polynomial functions whose coefficients are recorded in the data memory; and/or
(c) by way of a neural network mapping function.

For example, complex impedance measurement using the sensor 200 over a frequency range from 100 kHz to 10 MHz generates a complex sequence of impedance measurements a function of frequency. Potentially, a given impurity ion resulting from a metallic salt present in the urea solution can influence the complex impedance at several spot frequencies in the frequency range. Interpreting the complex impedance can be convoluted especially when there is noise present due to movement of a vehicle with which the apparatus 100 is installed. By using the complex impedance measurement at various spot frequencies as input to a neural network algorithm, the algorithm can be adapted to recognize different types of urea solution and their associated qualities. Beneficially, the algorithm is also furnished with data from one or more of the sensors 180A, 180B, 190. Parameters employed in the data processing unit 230 for performing the aforementioned mapping are beneficially dynamically alterable by data instructions sent to the data processing unit 230. Such alterable functionality enables the apparatus 100 to be dynamically updated with parameters which enable it to most accurately identify various types of impurity. For example, in an agricultural environment, there may be a spate of cases where specific types of impure low-grade urea are used for Adblue, DEF to save money, but which cause unexpected environmental damage by way of engine emissions via their exhaust treatment systems. The apparatus 100 beneficially needs to be adaptable to identify most effectively such spates of abuse. Optionally, operating parameters of the apparatus 100 can be updated by supplying external data to the data processing unit 230 for enabling the apparatus 100 to adapt dynamically to different types of solution.

When the apparatus 100 is mounted to a tank of a vehicle, movement of the vehicle in operation influences liquid in the tank, for example causing it to slosh around the tank and thereby resulting in measurements executed by the sensors 190, 200 to be temporally varying. In consequence, the apparatus 100 is optionally operable to average its measurements over a period of time. Optionally, the period of time over which averaging occurs is dynamically variable in response to data instructions sent to the data processing unit 230 of the apparatus 100.

Modifications to embodiments of the invention described in the foregoing are possible without departing from the scope of the invention as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:

1. An apparatus (100) for measuring the quality of a urea solution in a tank, wherein at least a portion of said apparatus is inserted in said tank, the apparatus comprising,
    a configuration of sensors (180, 190, 200), wherein said sensors (180, 190, 200) are spatially distributed for measuring mechanical and electrical properties within a volume of said urea solution, said measurements of mechanical and electrical properties being influenced by components present in the urea solution which influence the quality of the urea solution, and
    a data processing arrangement (230) for processing said measurements of said mechanical and electrical properties for generating output data (120) indicative of the quality of said urea solution.

2. An apparatus (100) as claimed in claim 1, wherein said configuration of sensors (180, 190, 200) includes acoustic and conductivity sensors (190, 200) for measuring mechanical and electrical properties respectively, said sensors (190, 200) being spatially deployed spaced apart within said apparatus (100).

3. An apparatus (100) as claimed in claim 1, wherein said sensors (180,190, 200) include a thermometer for measuring a temperature (T) of said urea solution, and for providing said data processing arrangement (230) data corresponding to said temperature (T) for use in computing said quality of said urea solution.

4. An apparatus (100) as claimed in claim 2, wherein said sensors (180,190, 200) include a thermometer for measuring a temperature (T) of said urea solution, and for providing said data processing arrangement (230) data corresponding to said temperature (T) for use in computing said quality of said urea solution.

5. An apparatus (100) for measuring the quality of a urea solution in a tank, wherein at least a portion of said apparatus is inserted in said tank the apparatus comprising,
    a configuration of sensors (180, 190, 200), wherein said sensors (180, 190, 200) are spatially distributed for measuring mechanical and electrical properties within a volume of said urea solution, said measurements of mechanical and electrical properties being influenced by components present in the urea solution which influence the quality of the urea solution, and
    wherein said configuration of sensors (180, 190, 200) includes an electrical conductivity sensor for measuring an electrical conductivity of the urea solution, said conductivity sensor including a configuration of electrodes (720) disposed in a flow tunnel (700, 710) for receiving the urea solution, said flow tunnel (700, 710) being operable to electrically screen said configuration of electrodes from external influences spatially outside said tunnel (700, 710), and
    a data processing arrangement (230) for processing said measurements of said mechanical and electrical properties for generating output data (120) indicative of the quality of said urea solution.

6. An apparatus (100) as claimed in claim 5, wherein said configuration of electrodes (720) includes electrodes disposed in a linear arrangement along said flow tunnel (700, 710).

7. An apparatus (100) as claimed in claim 6, wherein an outer set of electrodes (P1) near ends of the flow tunnel (700, 710) are operable to be excited to generate an interrogating electric field within said tunnel (700, 710) and an inner set of electrodes (P2) near a central region of the flow tunnel (700, 710) are operable to generate a received signal for conveying to the data processing arrangement (230).

8. An apparatus (100) as claimed in claim 5, wherein said configuration of electrodes (P1, P2) includes at least one of: stainless steel electrodes, carbon electrodes, silver electrodes.

9. An apparatus (100) as claimed in claim 6, wherein said configuration of electrodes (P1, P2) includes at least one of stainless steel electrodes, carbon electrodes, silver electrodes.

10. An apparatus (100) as claimed in claim 7, wherein said configuration of electrodes (P1, P2) includes at least one of: stainless steel electrodes, carbon electrodes, silver electrodes.

11. An apparatus (100) as claimed in claim 1, wherein said data processing arrangement (230) is operable to apply at least one of alternating (a.c.) signals and static (d.c.) signals to said configuration of electrodes (720) when in operation for determining at least one of static conductivity and complex conductivity of said urea solution for use in determining its quality.

12. An apparatus (100) as claimed in claim 1, wherein said configuration of sensors (180,190, 200) includes an acoustic sensor (180) including an acoustic transducer arrangement (530) disposed in a spaced apart manner from a corresponding acoustic reflector (510), wherein the transducer arrangement (530) is operable to generate one or more acoustic pulses which propagate through the urea solution, are reflected from the reflector (510) and are subsequently received back at the transducer arrangement (530) for generating a received signal for the data processing arrangement (230) to process for determining a density of the urea solution.

13. An apparatus (100) as claimed in claim 1, wherein said apparatus (100) further includes a mounting flange (110) for mounting said apparatus (100) to a urea solution tank, a heater arrangement (130,140) for heating said urea solution, and a urea solution level sensing arrangement (150, 160) for sensing a surface height of the urea solution relative to said apparatus (100).

14. A method of measuring the quality of a urea solution by using an apparatus (100), said method comprising:
    (a) inserting at least a portion of said apparatus into said urea solution;
    (b) measuring using a configuration of sensors (180, 190, 200) of said apparatus (100), wherein said sensors (180, 190, 200) are spatially distributed for measuring mechanical and electrical properties within a volume of said urea solution, said measurements of mechanical and electrical properties being influenced by components present in the urea solution which influence the quality of the urea solution; and (c) processing using a data processing arrangement (230) said measurements of said mechanical and electrical properties for generating output data (120) indicative of the quality of said urea solution.

\* \* \* \* \*